(12) United States Patent
Narkunan et al.

(10) Patent No.: US 6,723,849 B1
(45) Date of Patent: Apr. 20, 2004

(54) PROCESS FOR MAKING CAMPTOTHECIN DERIVATIVES

(75) Inventors: Kesavaram Narkunan, San Antonio, TX (US); Harry Kochat, San Antonio, TX (US); Xinghai Chen, San Antonio, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 10/627,444

(22) Filed: Jul. 25, 2003

Related U.S. Application Data

(60) Provisional application No. 60/421,549, filed on Oct. 25, 2002.

(51) Int. Cl.$^7$ .................. C07D 491/22; C07D 491/147
(52) U.S. Cl. ............................................ 546/14; 546/48
(58) Field of Search ..................................... 546/14, 48

(56) References Cited

U.S. PATENT DOCUMENTS 6,194,579 B1 * 2/2001 Hausheer ..................... 546/48

* cited by examiner

*Primary Examiner*—Charanjit S. Aulakh
(74) *Attorney, Agent, or Firm*—Thomas J. Dodd

(57) ABSTRACT

A process for synthesizing highly lipophilic derivatives of camptothecin. The process includes reacting dissolved, underivatized camptothecin with an aldehyde in a modified Minisci-type alkylation reaction to produce 7-substituted derivatives of camptothecin.

9 Claims, No Drawings

PROCESS FOR MAKING CAMPTOTHECIN DERIVATIVES

CROSS-REFERENCE TO RELATED APPLICATIONS

This application claims the benefit of U.S. Provisional Application, Ser. No. 60/421,549, filed Oct. 25, 2002.

FIELD OF THE INVENTION

This invention relates to a process for making certain camptothecin derivatives and will have application to a semi-synthetic process for making large quantities of highly lipophilic camptothecins that include one or more silicon atoms in the structure.

BACKGROUND OF THE INVENTION

Highly lipophilic camptothecin derivatives (HLCDs), particularly those containing silicon-based moieties, are effective anticancer drugs. One of the most noted of the silicon-containing HLCDs has the IUPAC name (4S)-4-ethyl-4-hydroxy-11-[2-(trimethylsilyl)ethyl]-1H-pyrano[3':4':6,7]indolizino[1,2-b]quinoline-3,14(4H,12H)-dione, and has also referred to as 7-(2'-trimethylsilyl)ethyl camptothecin (also known as Karenitecin™ and BNP1350), currently in human clinical trials in the United States and internationally. U.S. Pat. No. 5,910,491 and others describe the compositions, formulations, and processes for making Karenitecin™ and other related HLCDs.

The currently known most preferred process for making Karenitecin™ is described and claimed in U.S. Pat. No. 6,194,579 (the '579 patent), incorporated herein by reference. In the '579 patent, Karenitecin™ and other silicon-containing HLCDs are manufactured by reacting camptothecin with a TMS-aldehyde and a strong oxidizing agent (hydrogen peroxide is preferred) in the presence of a metal sulfate to effect a Minisci-type alkylation. As described in the '579 patent, the resulting alkylation moiety contained one less carbon atom than the TMS-aldehyde, a typical characteristic of the Minisci alkylation.

The prior process for synthesizing Karenitecin was efficient in small-scale (gram) production, but improvements were necessary to enable efficient larger scale production. Improvements were needed primarily to boost yields (and accordingly reduce impurities), and to simplify the purification process. The prior process resulted in 50%–60% yields and had to be purified by column chromatography.

Other prior processes for synthesizing HLCDs can be found in U.S. Pat. No. 6,150,343 and others. These prior processes utilize a total synthesis route to synthesize the camptothecin skeleton. Due to the low yields and higher costs of these methods, they are considered impractical and inefficient for conducting large-scale synthetic operations.

SUMMARY OF THE INVENTION

The synthetic process of this invention is adapted to produce HLCDs having the following structure I:

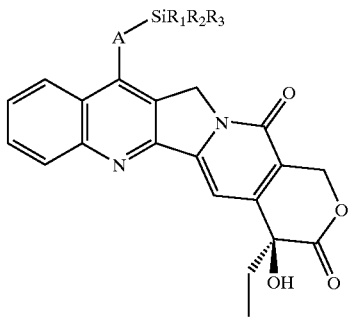

wherein

A is —$(CH_2)_n$— where n is 1 to 6;

and $R_1$, $R_2$, and $R_3$ are individually lower alkyl or aryl.

The process is essentially a one-step process for synthesizing the preferred compounds from camptothecin. As is well known, camptothecin can be isolated from the bark of the *Camptotheca accuminata* tree, which grows primarily in Asia. The active form of camptothecin is the (S)-stereoisomer shown above, which can be purchased as a commercial product in substantially pure form from any of a number of commercial sources in China and India.

In the process of this invention, camptothecin is dissolved in a strong acid. Oxidizing agent is added to this solution, which is then added to the solubilized aldehyde reagent/metal sulfate solution. The aldehyde is dissolved in a non-polar aprotic solvent, which both enhances the solubility of the aldehyde and minimizes the possibility of solvent reaction with the camptothecin.

Further, the mode of addition of reagents has been altered from the previous method. 30% sulfuric acid is utilized initially to solubilize the camptothecin, rather than being added to the camptothecin/aldehyde solution. This change limits the exothermic changes of the prior process, which decreases the possibility of polymerization of the aldehyde. Yields and purity are highly improved over prior processes for synthesizing Karenitecin.

Finally, extraction and other final processing steps were improved, and allow the process to be scaled up to make larger quantities (>50 g) of Karenitecin. The preferred process calls for extraction with dichloromethane, followed by washing of the extract, then recrystallizing the crude product from the extract using dimethyl formamide (DMF).

DETAILED DESCRIPTION OF THE INVENTION

The preferred embodiments depicted below are not intended to be exhaustive or to limit the invention to the precise forms disclosed. They have been chosen and described to explain the principles of the invention, and its application and practical use to thereby enable others skilled in the art to understand its teachings.

In this application, the term "lower alkyl" means a straight or branched chain hydrocarbon containing from one to six total carbon atoms. "Aryl means an aromatic ring system, fused or unfused, preferably from one to three total rings, with the ring elements consisting entirely of carbon atoms.

The process of this invention is employed to synthesize compounds of formula I, shown above. Preferred compounds synthesized by the process include those compounds where n is 1, 2 or 3, and $R_1$, $R_2$ and $R_3$ are methyl, tert-butyl or phenyl. The process is depicted in the following Schemes.

Scheme 1

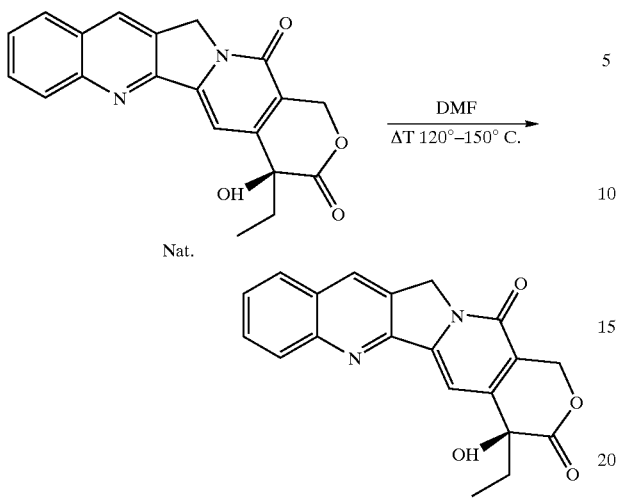

Scheme 1 illustrates the recrystallization of camptothecin from its natural product. The recrystallization is preferably carried out at elevated temperatures, in any organic solution that will dissolve camptothecin, most preferably N,N-dimethyl formamide. The end product is substantially pure (preferably no less than 90%, most preferably no less than 98%) S-camptothecin.

Scheme 2

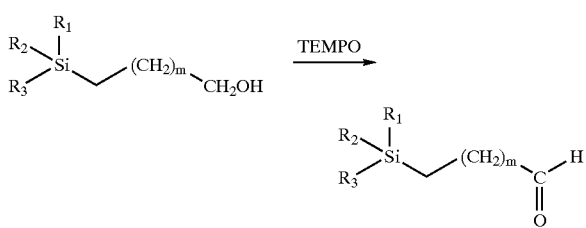

Scheme 2 illustrates the preparation of the aldehyde reactant by oxidation from the corresponding alcohol. In the Scheme, m is 0 to 5 and the alkylene chain linking the terminal silane to the alcohol (aldehyde) may be straight-chain or branched-chain, as desired. Preferably, m is 1 to 3, most preferably 1, and the most preferred end product is 3-trimethylsilyl-1-propanal.

The process shown in Scheme 2 is preferably a one-step, single pot process. The alcohol is generally available from commercial sources, as are the reagents. As shown, the alcohol is reacted with one or more oxidizing agents, such as sodium hypochlorite, hydrogen peroxide, and others, in the presence of a catalyst, such as 2,2,5,5-tetramethyl piperidino-1-oxo (TEMPO). The reaction is carried out at room temperature and generates highly pure (90%+) concentrations of the desired end product.

Scheme 3

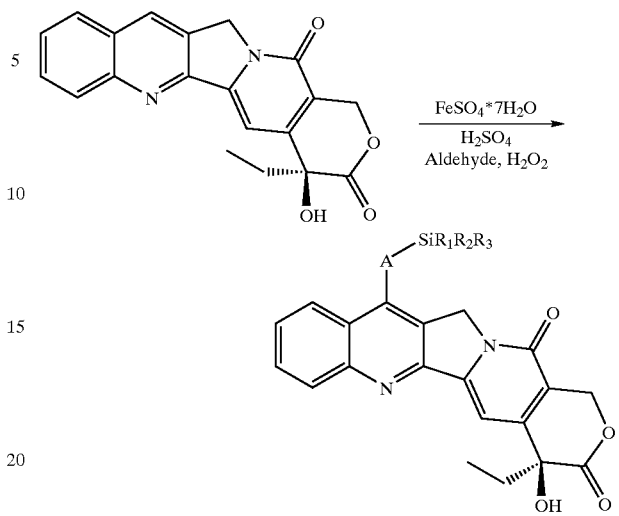

Scheme 3 illustrates the conversion of (S)-camptothecin to the desired formula I compound. The conversion is preferably achieved through a modified Minisci-type alkylation reaction. A Minisci-type alkylation utilizes aldehyde in the presence of hydrogen peroxide and metal sulfate to effect an alkylation that is one carbon atom fewer than the aldehyde.

In the process of this invention, as depicted in Scheme 3, the modified Minisci-type alkylation provides for first mixing the aldehyde and the metal sulfate reagents in a strong acid solution, and agitating to produce a homogenous solution. To the mixture is added a nonpolar, aprotic co-solvent, preferably an ether or diether, most preferably 1,2-dimethoxy ethane (Monoglyme®). The cosolvent is preferably non-reactive with the other reagents and inhibits the formation of undesired side products often found in a Minisci-type alkylation reaction. In the prior processes to synthesize formula I compounds, the major undesired side product included the N-oxide form of camptothecin, and resulted in low yields and purity.

After premixing the aldehyde and metal sulfate, camptothecin from Scheme 1 is dissolved in a strong acid, and a strong oxidizing agent, preferably hydrogen peroxide. The camptothecin solution is then slowly added to the aldehyde/metal sulfate solution, and the temperature controlled. Preferred addition times depend upon the amount, generally between 10 mL/min to 2000 mL/min, most preferably between 25 mL/min to 500 mL/min. The temperature is controlled by conventional means, and is preferably kept below about 50° C., most preferably below 40° C. Additional oxidizing agent is preferably added to the mixture after the initial addition of the camptothecin/oxidizing agent solution. The formula I compound is then isolated and purified by recrystallization.

The following specific examples illustrate the process, but are not to be considered as limiting the invention to the precise reagents, steps or conditions depicted.

EXAMPLE 1

(S)-Camptothecin

To a glass reactor equipped with reflux condenser, mechanical agitator, nitrogen purging valve, heating-cooling skid and solid charging inlet, is added 50 g of naturally occurring camptothecin. 0.5 L of dimethyl formamide is added to the reactor and heated to approximately 150° C. to completely dissolve the suspended camptothecin into dimethyl formamide while maintaining agitation. Once the dissolution is completed, the content of the reactor is allowed to cool to ambient temperature with slow stirring. The recrystallized camptothecin is then filtered through a coarse sintered funnel under industrial vacuum. The wet cake thus obtained is then washed with 25 mL of t-butyl methyl ether. The product is then dried inside an oven at 60° C. for approximately 24 hours. The net weight of the resulting pale yellow solid is recorded, and checked for purity. Limit=not less than 98% by area.

EXAMPLE 2

3-trimethylsilyl-1-propanal 3.37±0.1 L Methylene Chloride was added to a 12 L flask and agitation was initiated. To the same flask is charged 0.15±0.05 kg of 3-trimethylsilyl-1-propanol. 1.79±0.1 g TEMPO (Tetramethyl piperidenyloxy free radical initiator), 9±1 g sodium bromide and 2.07±0.1 L of deionized water was added to the flask. The mixture was agitated vigorously for at least 15 minutes.

In a separate container, 0.95±0.1 L deionized water and 0.18±0.1 kg Sodium bicarbonate were added. The contents were stirred and allowed to dissolve as much as possible. To the same container was added 3.79±0.5 kg of 4% sodium hypochlorite. The bicarbonate solution was transferred by an addition funnel to the 12 L flask over at least 45 minutes, and the solution was agitated for approximately 10 minutes. Once the color of the solution changed from light brown to clear, we proceeded to the next step.

At this point, agitation was terminated and the layers allowed to separate for at least 5 minutes. Once reaction is completed, the aqueous layer was discharged and the organic layer saved for subsequent work-up.

To a glass reactor vessel, 0.3±0.1 kg of sodium thiosulfate and 1.12±0.1 L deionized water was added and agitated vigorously. The saved organic layer from the previous step was added back into the 12 L flask followed by the thiosulfate solution. Agitation was halted and the layers allowed to separate for at least 5 minutes. The bottom organic layer was collected in a clean container and washed with 1.1±0.1 L of deionized water, then dried over ⁻0.43±0.1 kg sodium sulfate. The sodium sulfate was filtered onto a fritted Buchner funnel, and the solvent removed at less than 30° C. under vacuum. The net weight of the resulting oil was recorded, and GC and NMR analysis conducted to verify the title product. Purity by GC is not less than 90% by area.

EXAMPLE 3

7-(2'-trimethylsilyl)ethyl camptothecin 20 g of iron sulfate heptahydrate was dissolved in 125 mL of 30% sulfuric acid, taken up in a 4 L three neck round bottom flask, and stirred for 20 minutes at room temperature. A solution of 48 g of 3-trimethylsilyl-1-propanal in 500 mL of Monoglyme was then added dropwise into the flask and stirred for 15 minutes. To the above mixture was slowly added (total of 30 minutes) a solution containing 25 g of camptothecin, 1375 mL of 30% sulfuric acid and 8.1 mL of 30% hydrogen peroxide. The solution was stirred for one hour at room temperature and another 24.3 mL of hydrogen peroxide was added over a 30 minute time period. The solution was then allowed to stir overnight for at least 6 hours. Time of actual agitation was approximately 16 hours.

The reaction mixture was then washed with hexanes (3×250 mL), and the aqueous portion was collected and returned to the flask, while the organic hexanes were discarded. The mixture was then extracted with methylene chloride (3×1250 mL). The solvent was then evaporated under vacuum, with the temperature held at 40° C. or below.

After extraction, the crude product was added to a vessel containing 30 mL of N,N-dimethyl formamide per gram of crude product. The resulting slurry was heated to 120° C. until all of the solid mass dissolved. The solution is then allowed to cool slowly to 25° C., and the recrystallized title product is filtered through a Buchner funnel. The wet product was then dried in an oven at 60° C. for 48 hours. 12.45 g of the title product were produced and verified by various analytical methods.

$^1$H NMR (300 MHz) 8.27 (d, J=7.8 Hz, 1H), 8.05 (d, J=7.8 Hz, 1H), 7.84–7.60 (m, 3H), 5.76 (d, J=16.2 Hz, 1H), 5.31 (d, J=16.5 Hz, 1H), 5.25 (s, 2H), 3.20–3.00 (m, 2H), 2.00–1.80 (m, 2H), 1.04 (t, J=7.5 Hz, 3 H), 1.00–0.90 (m, 2H), 0.18 (s, 9H).

Mass Exact for $C_{25}H_{28}N_2NaO_4Si$ is 471.1716 and found 471.1699.

The above description does not limit the invention to the reagents, amounts, steps, conditions or equipment identified, and may be modified within the scope of the following claims.

What is claimed is:

1. A process for synthesizing camptothecin derivatives having the formula:

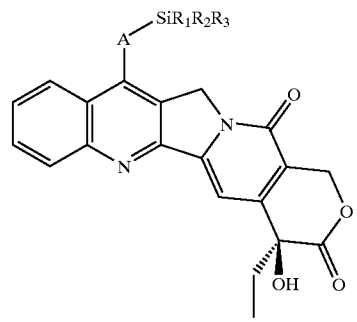

where

A is —$(CH_2)_n$— where n is 1 to 6;

and $R_1$, $R_2$, and $R_3$ are individually lower alkyl or aryl, the process comprising the steps of:
  a) providing a quantity of substantially pure camptothecin, and dissolving in a strong acid;
  b) adding a strong oxidizing agent to the camptothecin and strong acid solution to form a reaction mixture, then adding the reaction mixture to a vessel containing:
    i) an aldehyde having the formula $R_1R_2R_3$Si—$(CH_2)_n$CHO in sufficient quantities to react with the reaction mixture;

ii) a nonpolar, aprotic solvent; and
iii) an iron salt;

c) agitating the vessel for a predetermined time to produce the formula I compound.

2. The process of claim 1 wherein the strong acid is sulfuric acid, the strong oxidizing agent is hydrogen peroxide, the iron salt is hydrated iron sulfate and the nonpolar aprotic solvent is a diether.

3. The process of claim 2 wherein the diether is 1,2-dimethoxyethane.

4. The process of claim 1 wherein n is 2 and $R_1R_2R_3$ are all methyl.

5. The process of claim 1 wherein n is 2.

6. The process of claim 1 and a purification step d) of recrystallizing the formula I compound directly from a second nonpolar aprotic solvent.

7. The process of claim 6 wherein the second nonpolar aprotic solvent is N,N-dimethyl formamide.

8. The process of claim 1 wherein additional quantities of strong oxidizing agent are added to the vessel after addition of the reaction mixture.

9. The process of claim 1 wherein step c) includes agitating the vessel for at least 6 hours.

* * * * *